United States Patent
Kingsford et al.

(10) Patent No.: US 6,851,161 B2
(45) Date of Patent: Feb. 8, 2005

(54) SEALING CLOSURES

(75) Inventors: Howard A. Kingsford, Amherst, NH (US); William H. Shepard, Amherst, NH (US); Paul A. Dandurand, Manchester, NH (US)

(73) Assignee: Velcro Industries B.V., Curacao (AN)

( * ) Notice: Subject to any disclaimer, the term of this patent is extended or adjusted under 35 U.S.C. 154(b) by 0 days.

(21) Appl. No.: 10/263,227

(22) Filed: Oct. 2, 2002

(65) Prior Publication Data

US 2003/0061692 A1 Apr. 3, 2003

Related U.S. Application Data

(63) Continuation of application No. PCT/US01/10620, filed on Apr. 3, 2001.
(60) Provisional application No. 60/194,221, filed on Apr. 3, 2000.

(51) Int. Cl.[7] ............................................. A44B 18/00
(52) U.S. Cl. ..................... 24/306; 443/450; 443/452
(58) Field of Search ...................... 24/442–456, 30.5 R, 24/30.5 P; 383/61.2, 61.3, 63, 68, 59; 428/100; 264/167

(56) References Cited

U.S. PATENT DOCUMENTS

| 3,282,493 A | 11/1966 | Kamins et al. |
| 3,338,285 A | 8/1967 | Jaster |
| 3,403,429 A * | 10/1968 | Smith .......................... 24/306 |
| 3,446,420 A | 5/1969 | Rinecker |
| 3,464,094 A | 9/1969 | Mates |
| 3,565,147 A | 2/1971 | Ausnit |
| 3,655,118 A | 4/1972 | Rinecker |
| 3,827,472 A | 8/1974 | Uramoto |
| 4,337,889 A | 7/1982 | Moertel |
| 4,426,816 A * | 1/1984 | Dean et al. .................... 52/202 |
| 4,578,813 A | 3/1986 | Ausnit |
| 4,601,694 A | 7/1986 | Ausnit |
| 4,617,683 A * | 10/1986 | Christoff ....................... 383/63 |
| 4,637,063 A | 1/1987 | Sullivan et al. |
| 4,658,433 A | 4/1987 | Savicki |
| 4,665,552 A | 5/1987 | Lems et al. |
| 4,796,300 A | 1/1989 | Branson |
| 5,009,828 A | 4/1991 | McCree |
| 5,345,659 A | 9/1994 | Allan |
| 5,470,156 A | 11/1995 | May |
| 5,474,382 A | 12/1995 | May |
| 5,489,252 A | 2/1996 | May |
| 5,509,735 A | 4/1996 | May |
| 5,542,766 A * | 8/1996 | Cadwallader ................. 383/63 |
| 5,551,127 A | 9/1996 | May |
| 5,605,594 A | 2/1997 | May |
| 5,647,671 A | 7/1997 | May |
| 5,725,312 A | 3/1998 | May |
| 5,729,876 A | 3/1998 | Johnson |
| 5,816,709 A | 10/1998 | Demus |
| 5,887,980 A | 3/1999 | May |
| 5,893,645 A | 4/1999 | May |
| 5,904,425 A | 5/1999 | May |
| 6,209,177 B1 * | 4/2001 | Murasaki ...................... 24/452 |

* cited by examiner

Primary Examiner—James R. Brittain
(74) Attorney, Agent, or Firm—Fish & Richardson P.C.

(57) ABSTRACT

A reclosable closure consists of two longitudinally continuous strips and which, when facially engaged, are held together by hook and loop fastening principles. The inner side of one strip has two fields of hook-engageable loops, separated by a female seal profile portion. The inner side of the other strip has two fields of molded hook elements arranged to engage the loops to hold the closure in its closed condition, and a central male seal profile portion for engaging the female seal profile portion to form a seal when the closure is closed. Another reclosable closure is held together by hook and loop fastening principles and includes a resilient bead that is compressed between opposing sides of the closure, or between spaced rails of an opposing side of the closure, when the hooks and loops of the closure are engaged. The closure is useful, for example, as a bag closure.

27 Claims, 9 Drawing Sheets

SEALING CLOSURES

CLAIM OF PRIORITY

This application claims priority under 35 USC §120 to and is a continuation of PCT/US01/10620, filed Apr. 3, 2001, which claims priority from U.S. Patent Application Ser. No. 60/194,221, filed on Apr. 3, 2000, the entire content of both of which are hereby incorporated by reference.

BACKGROUND

This invention relates to reclosable, sealable fasteners, such as for bag closures.

Extruded interlocking profile fasteners, such as those known to be marketed under the trade name "ZIPLOC", have been employed as closures for bags and other packaging for many years. Such closures have the advantage of providing a reasonably reliable seal across the bag opening, as well as holding the two sides of the bag opening together. Furthermore, they are readily produced by known extrusion methods, their principle of engagement being the interlocking of mating longitudinal features having extrudable, complementary shapes. Thus, such fastening is sometimes referred to as 'rib and groove' fastening. Forming the head of the rib to be wider than the neck of the groove creates a 'snap' engagement (during which one or both of the profiles resiliently deforms) to retain the rib within the groove until pulled out. A relatively tight fit of the rib within its groove can provide an effective seal. Rib and groove closure strips and the film forming the sides of their associated bags are commonly made separately and then joined.

More recently, advancements in the production and design of hook and loop fasteners have resulted in cost-effective alternatives to rib and groove fastening for releasably securing bag openings in a closed condition. The principle of engagement of hook and loop fasteners involves the statistical engagement of a field of hooks, or male-type fastener elements, with a field of loops or fibers. Thus, hook and loop fasteners do not require precise alignment for closure. Also, face-to-face hook and loop closures form many small passages between the engaged fields of hooks and loops, enabling air (and, in some cases, liquids) to migrate across the closure. For some applications, such free ventilation is desirable. In some other applications, however, a liquid or air-tight seal, or an advantageously lower leak rate, would be preferred.

SUMMARY

The invention features a hook and loop closure incorporating a seal that provides a seal between the two sides of a bag opening when the hooks and loops of the closure are engaged. In some cases, the seal comprises complementary profiles that may, in certain constructions, be adapted to interlock when the two sides of the closure are pressed together. In some other cases, the seal comprises a resilient material that is compressed against an opposing side of the closure when the hooks and loops are engaged.

In some embodiments, the hooks and loops of the closure are placed in separating tension when engaged to generate seal-enhancing compression between engaged surfaces of the seal.

In some embodiments, the hook and loops of the closure hold complementary surfaces of the seal in adjacent relation to form a tortuous leak path across the seal.

Because sealing compression is maintained by tension in the engaged hook and loop elements, which also hold the closure in its engaged state, an interference or snap fit between the mating features of the seal is not required for many basic applications. Closure is effected without precise alignment, and the closure is readily formed of materials compatible with standard bag films, such as nylon, polyester, and either low-density or high-density polyethylene. The closure can be formed in a continuous process with equipment and processes known in the hook and loop closure industry, as described herein, in a cost-effective manner.

These fastener strips are particularly useful for bag closures, such as for bags containing viscous fluids that would undesirably seep through hook-and-loop closures.

In some embodiments the male and female portions of the seal are configured to have multiple sealing surfaces that are held together by tension in the hook-loop interface to produce a liquid-tight seal.

In some other embodiments, the male and female seal portions are configured to form a tortuous leak path between the mating fastener strips, for controlling leakage through the seal or for permitting leakage of one substance (e.g., air or gas) while preventing leakage of another substance (e.g., water or liquid).

Preferably, the effective sealing surfaces of the seal portion are inclined at an angle (e.g., each inclined at complementary angles or at selectively dissimilar angles) to the bases of the fastener strips such that the effective width of the seal is greater than the actual width, as measured across the fastener product, of the sealing surfaces.

Thus, hook-loop fastening is advantageously wed to a mating profile seal, such that the hook-loop components of the fastener provide the major part of the opening resistance of the closure, spread out over the wide width of the hook and loop arrays, maintaining the seal portion of the closure in its engaged condition. The design of the seal need not, therefore, be constrained by the need to provide opening resistance, and the design of the hook-loop components need not be affected by the need to provide leakage protection. Furthermore, a method is provided for forming such dual nature fastener products in a continuous process in which at least a portion of the sealing surface is molded simultaneously with an array of hook elements.

In some embodiments, the sealing surfaces, the strip base and the hook elements are all formed of one stream of common resin, such that all have the same material properties. Alternatively, multiple resins may be introduced to the forming nip, such that the seal portions are formed of one material, such as a highly elastomeric material, with the hook elements formed of a stiffer material. Similarly, one side of the seal may be formed of different material than the other.

According to another aspect of the invention, a method of forming a fastener product includes molding a strip-form base of resin while integrally molding both an array of male fastener elements extending from a surface of the base and a longitudinal structure having a surface adapted to engage a surface of a mating fastener product to form a seal.

According to yet another aspect, a method of forming a fastener product includes molding a strip-form base of resin under pressure in a gap adjacent a rotating roll, while introducing to the gap a preformed bead of resilient material in a groove defined in the roll, such that the bead of resilient material is permanently bonded to the resin by pressure in the gap to the base in an area between parallel arrays of fastener elements.

The fastener elements may comprise either male fastener elements, or hook-engageable loops or fibers, or both.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
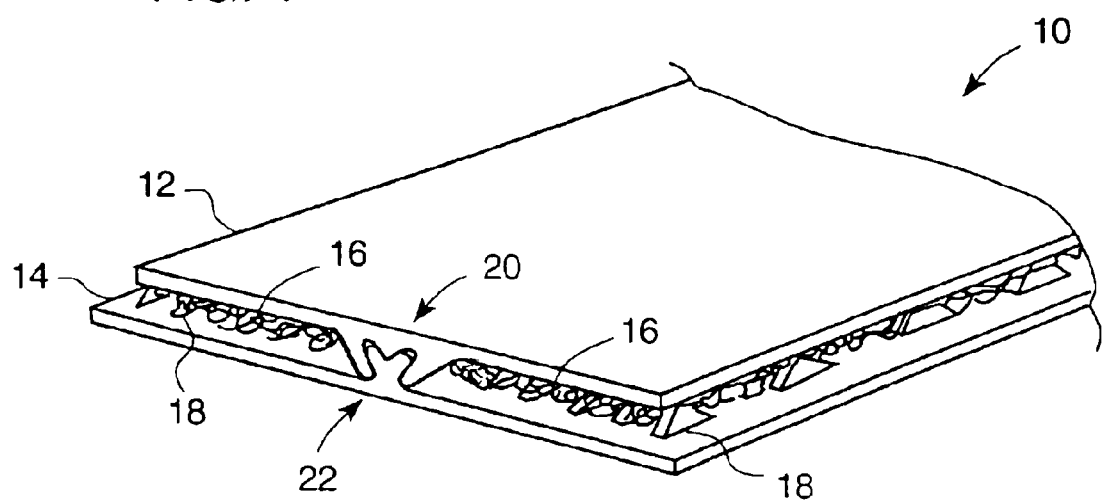
FIG. 1 is a perspective view of two engaged fastener strips.

Referring to FIG. 1, reclosable closure 10 consists of two longitudinally continuous strips 12 and 14 which, when facially engaged, are held together by hook and loop fastening principles. The inner side of strip 12 has two fields of hook-engageable loops 16, separated by a female seal profile portion 20. The inner side of strip 14 has two fields of molded hook elements 18 arranged to engage the loops 16 of strip 12 to hold closure 10 in its closed condition as shown, and a central male seal profile portion 22 for engaging female seal profile portion 20 to form a seal when the closure is closed. Closure 10 is useful as a bag closure in many applications, such as those described in U.S. Ser. No. 09/187,389, now U.S. Pat. No. 6,202,260 (incorporated herein by reference), in which more sealing is desired than is provided by hook and loop fastening. As taught in the incorporated reference, the two sides of the closure may be formed together as one continuous product, and then folded over onto itself to engage the loops of one half of the closure with the hooks of the other half of the closure. Alternatively, the two halves of the closure may be formed separately. A very limited width of the closure is shown to illustrate the shape of the seal portion. The width of the closure strips in many applications is 0.5 inch or more, with an overall engaged thickness of less than about 0.04 inch.

Figure 1A:
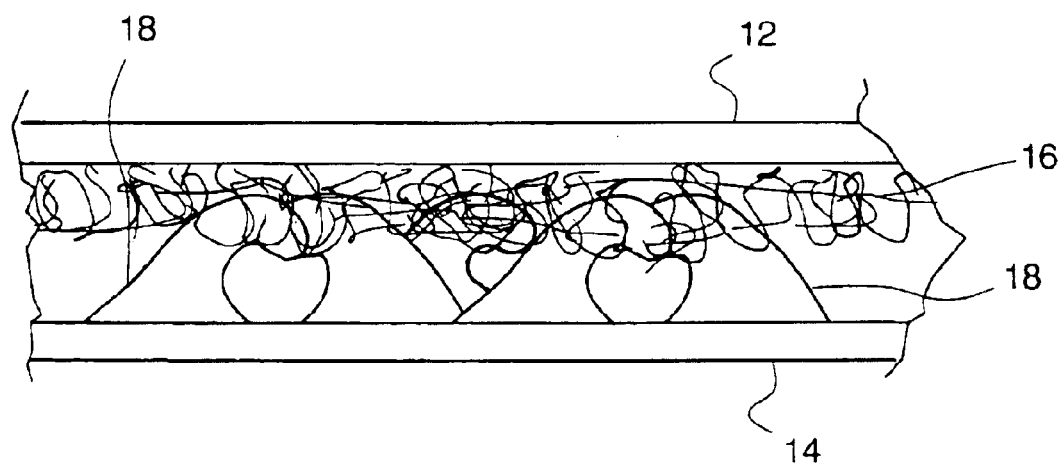
FIG. 1A is an enlarged side view of the engaged fastener strips.

FIG. 1A better illustrates the profiles of the molded hook elements 18, which are arranged in longitudinal rows along strip 14, and overhang the base of strip 14 in the direction of extent of the rows. The hooks 18 of adjacent rows face in opposite longitudinal directions. Each hook element 18 forms a crook for retaining individual fibers or loops 16 of strip 12. Various male fastening elements 18 may be employed as alternatives to hook shapes, such as mushrooms, palm trees, canted spikes or other loop-engageable form protruding from the base of strip 14. Furthermore, the fastening elements need not be formed in longitudinal rows, or face in the longitudinal direction of strip 14, or be integrally molded in the broadest aspects of the invention. The base thickness of each fastener strip is preferably on the order of 0.002 to 0.008 inch for many packaging applications.

Figure 2:
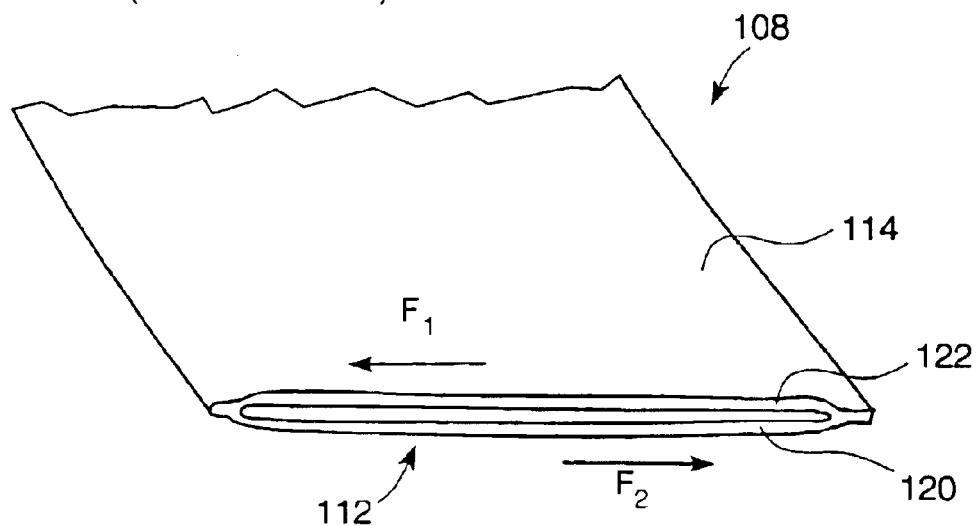
FIGS. 2–2A illustrate an opening mode of a rib and groove bag closure.
Figure 2A:
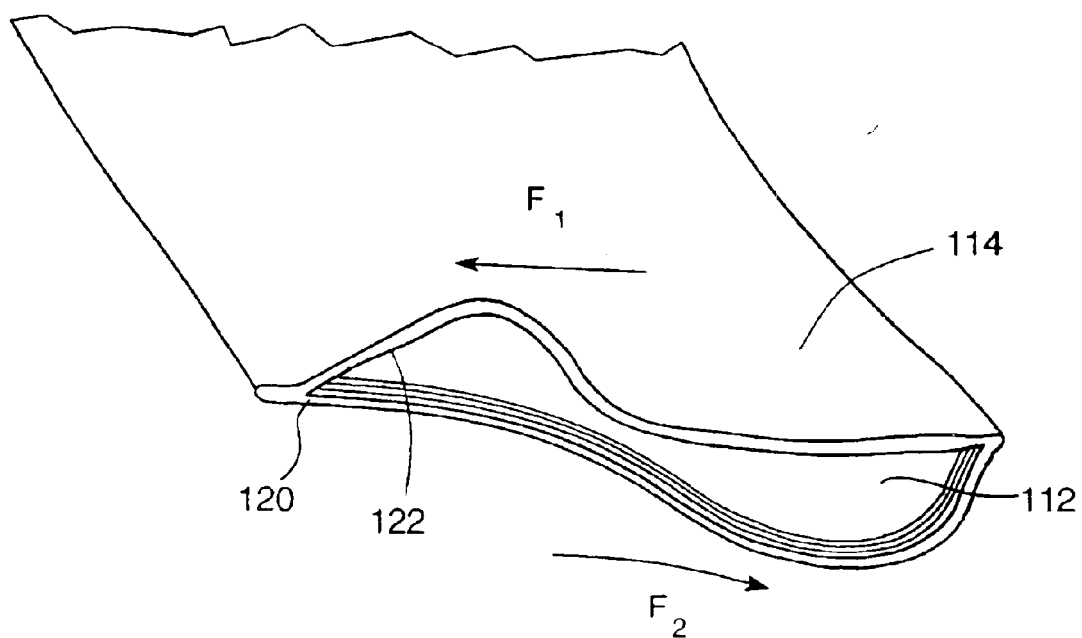

One advantage of hook and loop closures over rib and groove closures is that hook and loop closures resist longitudinal shear that can cause unwanted opening of rib and groove closures, as illustrated in FIGS. 2 and 2A. Bag 108 is sealed by engagement of rib 122 of first bag wall 114 with groove 120 of second bag wall 112. Rib 122 and groove 120 can be disengaged due to shear forces F1 and F2 acting along the bag walls 114 and 112, respectively, to slide rib 122 relative to groove 120 until the profiles separate near the edges of the bag (FIG. 2A). Hook and loop closures, on the other hand, resist such unwanted occurrences. The combination of hook and loop fasteners used in conjunction with sealing profile arrangements as described herein are particularly advantageous in that engagement of the hooks and loops provides resistance to shear forces acting on the closure strips (i.e., the hook and loop engagement prevents the closure strips from sliding relative to each other in a direction parallel to the sealing surfaces.

Figure 3:
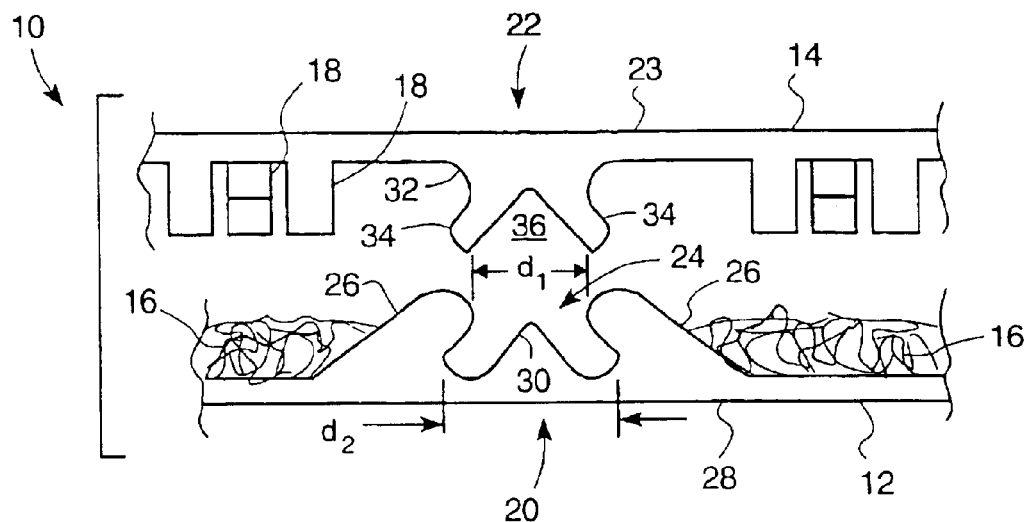
FIGS. 3–5 sequentially illustrate the engagement of the two fastener strips.
Figure 4:
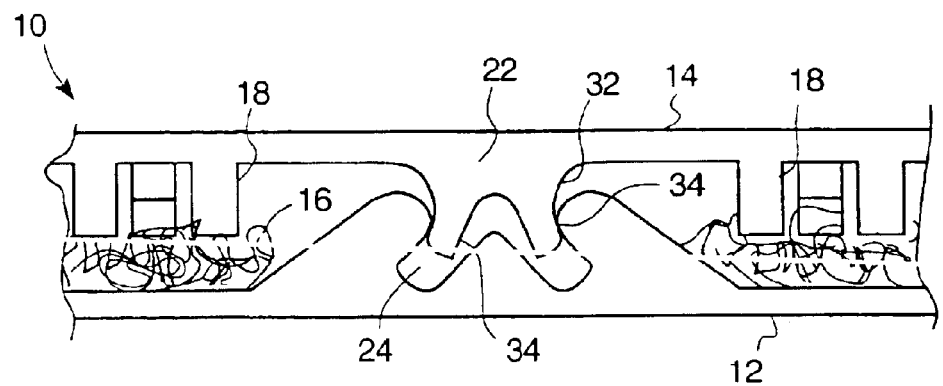
Figure 5:
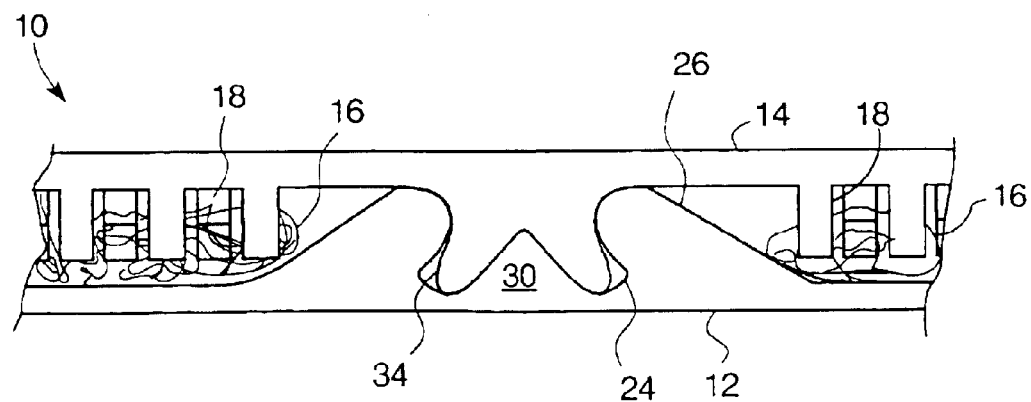

Referring to FIGS. 3 through 5, the two strips of closure 10 are engaged by bringing their inner sides together in face-to-face relation. Separated (FIG. 3), the hooks 18 of strip 14 are disengaged from the loops 16 of strip 12. The hook shape of hooks 18 is not apparent in this view, as the hooks are molded integrally with material of the base 23 of strip 14 to face in a longitudinal direction. In this unstressed state, female seal profile portion 20 forms a Y-shaped cavity 24 for receiving male seal profile portion 22. Longitudinal cavity or groove 24 is defined between two extending and opposing rails 26 integrally formed with plastic resin of the base 28 of strip 12. To facilitate pulling the molded rails 26 from their forming grooves, as discussed below, their thickness tapers from base to tip. Rails 26 may be described as being canted toward each other so as to form a Y-shaped groove, their minimum separation $d_1$ being less than their separation $d_2$ at their base. The indentation in the middle of Y-shaped cavity 24 is formed by a hump-shaped protrusion 30 of base 28 extending as a rib midway between rails 26. V-shaped longitudinal rib 32 of male seal profile portion 22 has two ears 34 separated by a valley 36. As strips 12 and 14 are moved toward each other, the ears 34 of rib 32 are deflected inward as rib 32 enters groove 24 (FIG. 4). At this point the hooks 18 and loops 16 of the two strips are in contact. Further relative movement of the two strips toward each other (FIG. 5) fully engages the fields of hooks and loops, with ears 34 projecting outwardly into the undercut regions of groove 24.

For some applications the complementing shapes of the rib and groove are selected such that, in the engaged state, the hooks and loops retain some tension, thereby creating compression between protrusion 30 and the ears 34 of rib 32 to enhance and maintain sealing. Having loops 16 of multiple heights and very flexible closure strip bases greatly enhances the development and maintenance of tension across the hook and loop interface. Alternatively, the mating profiles may be constructed such that one or the other is resiliently deformed during engagement, such as by selectively varying the angle of the mating surfaces with respect to the base, in order to provide a residual compression between the sealing surfaces until the closure is opened. Such compression may be resisted by the hook and loop interface or by other portions of the seal.

Figure 6:
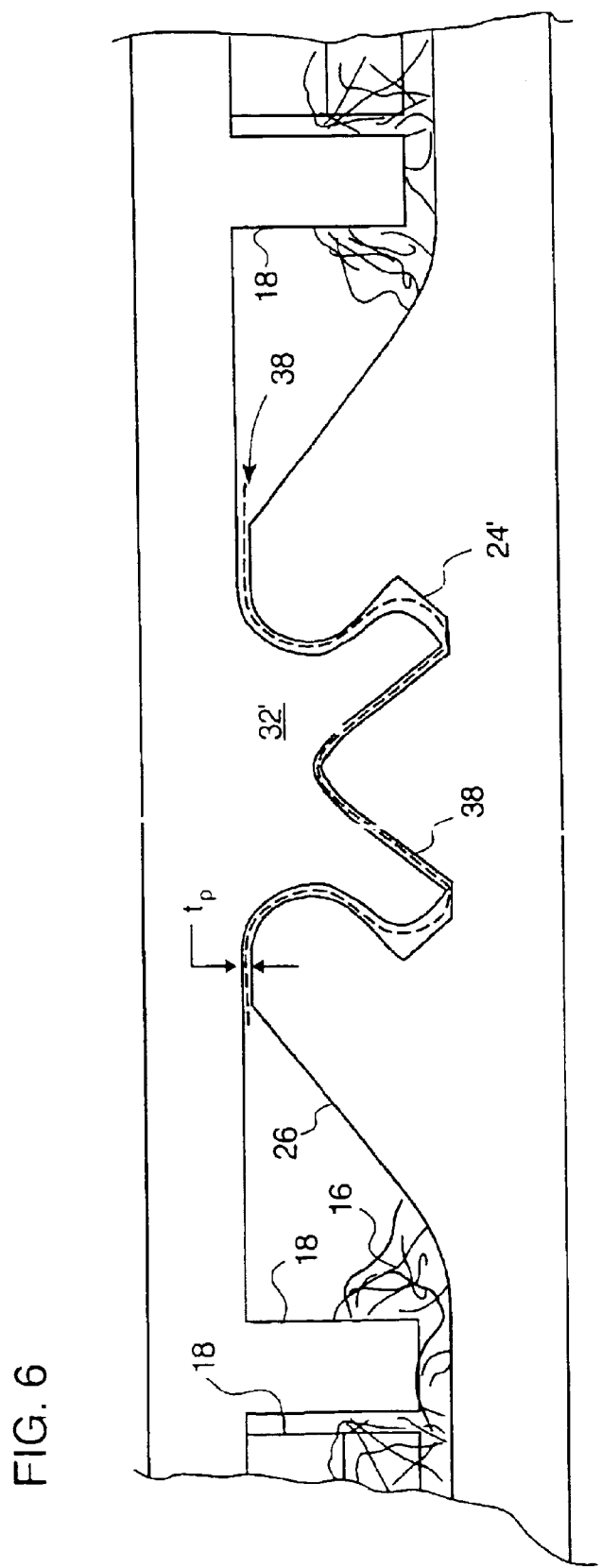
FIG. 6 is an enlarged end view of the seal portion of the engaged fastener strips.

For some other applications, however, a desired amount of sealing is obtained without maintaining compression across the seal portion of the closure. In FIG. 6, for example, rib 32' and groove 24' have been formed for a loose fit with the fields of hooks and loops engaged. Sealing in such cases is provided by the tortuous path 38 defined between the complementary profiles of the seal portion. Consistent forming of these features of the closure strip produces a reasonably predictable resistance to the flow of liquid through the seal, for controlled leakage or to enable gas ventilation while resisting liquid flow, and repeatable path thicknesses $t_p$ of 0.002 inch or less are achievable with current molding methods. As the resistance to flow is also affected by the overall length of path 38, it will be understood that multiple parallel ribs and grooves may be provided for enhanced flow resistance, and that the shape of the ribs and grooves may be modified to meet the needs of any given application.

Figure 7:
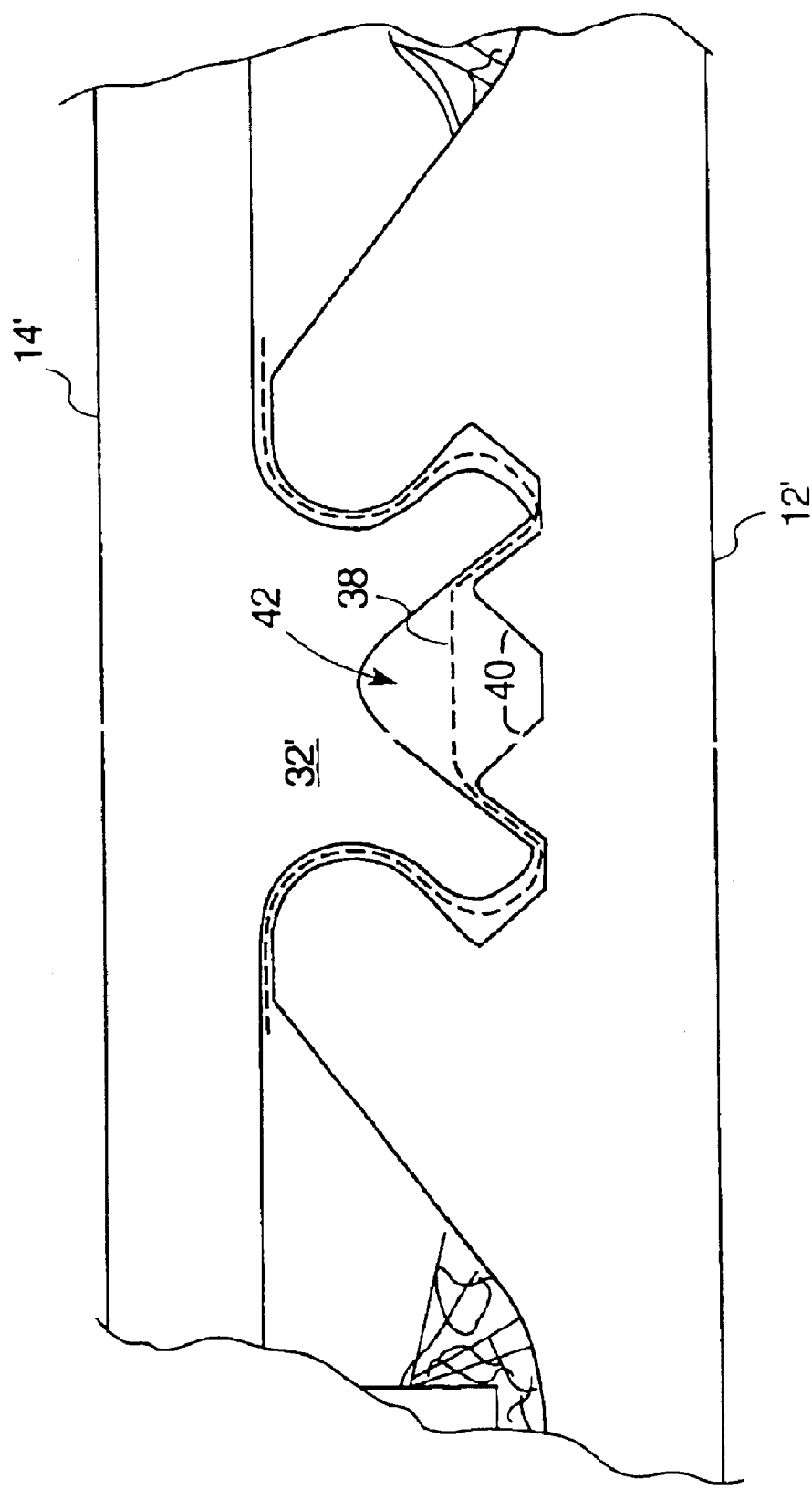
FIG. 7 is an enlarged end view of a second embodiment of the seal portion.

For example, FIG. 7 shows a modification in which the protrusion in the center of the groove has been replaced by two smaller protrusions 40, effectively shortening the length of leak path 38 across the sealing portion of the closure and providing an open longitudinal cavity 42 running along the engaged seal portion of the closure for collecting and retaining leakage, serving as a reservoir for air or liquid displaced by the engagement of the seal portion, etc. The configuration of FIG. 6 also provides greater flexibility, as cavity 42 provides space for the two fastener strips to flex with respect to one another.

Figure 8:
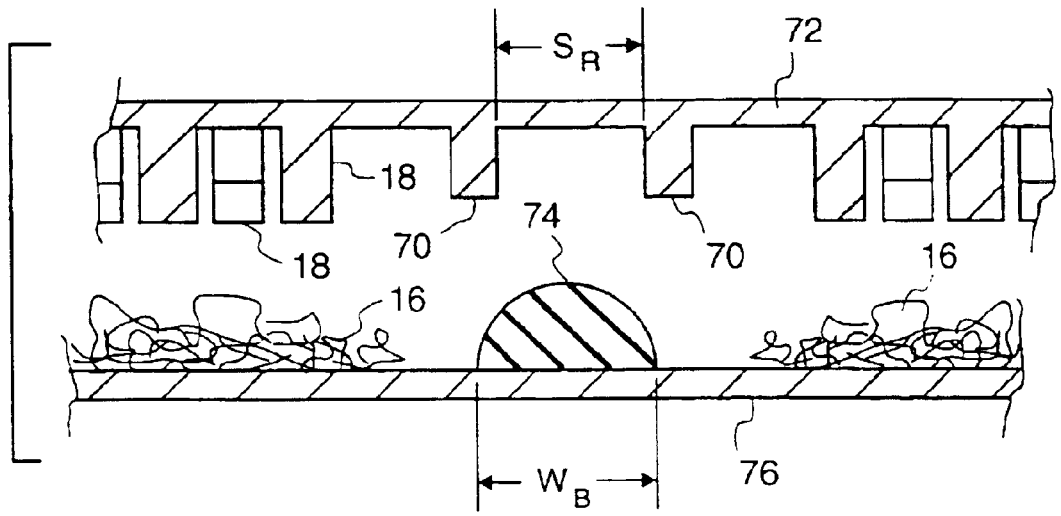
FIG. 8 is a transverse cross-sectional view of a closure with third embodiment of the seal arrangement.

Another seal arrangement is shown in FIG. 8. On one side of the closure, a pair of spaced rails 70 with opposing inner sides separated by a rail spacing $S_R$ preferably selected to be greater than the largest expected particle size of particulate material expected to be contained in the bag. Longitudinally continuous rails 70 are integrally molded with base 72 and hook elements 18 by appropriately shaped mold plates in the continuous molding process described below with respect to the first illustrated embodiment. Rails 70 need not be rectangular as shown, but may be appropriately shaped to present a desired sealing surface to the opposing side of the closure. On the opposing side of the closure a bead 74 of resilient material, such as a closed cell foam, is bonded to the base 76 of the closure and has a width $W_B$ greater than rail spacing $S_R$, such that interference between the bead and the rails produces a residual compression between rail and bead surfaces to form a cross-closure seal. In this construction, the bead material should be sufficiently resilient that, given the selected amount of interference between bead and rails, the seal will accommodate a reasonable amount of closure flexure and rail movement while maintaining a desired amount of sealing. One example of a resilient bead material is urethane foam.

Bead 74 may be jetted onto closure base 76 after the closure base has been molded in the process discussed below, or otherwise adhered to the closure base. Alternatively, the bead may be joined to resin of the base as the base is molded, as discussed below with respect to FIG. 15.

As an alternative construction for applications which are not intended to require any alignment for adequate sealing, rails 70 may be omitted and seal 74 arranged to seal against the flat surface of base 72 between arrays of hooks 18. As with the embodiments described above, tension across the hook and loop interface maintains compression across the seal. Thus, the functions of closure retention and closure sealing are performed by separate structures in the closure, with the hooks and loops retaining closure and the seal inhibiting leakage.

Figure 9:
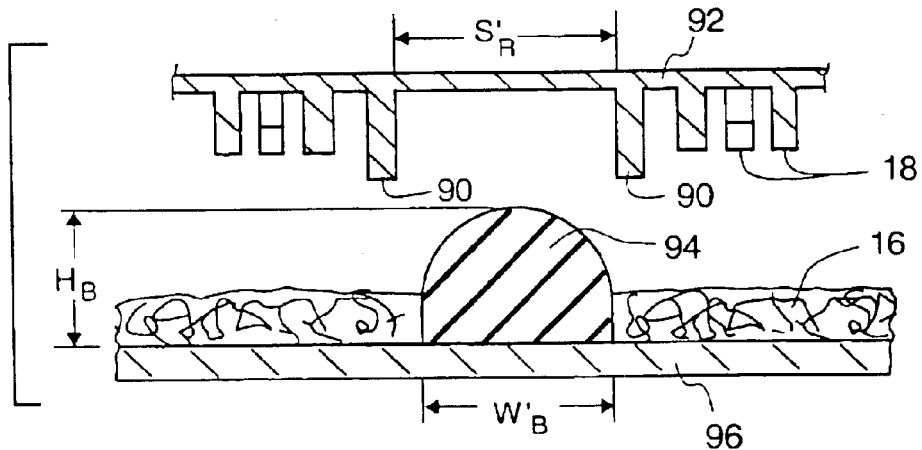
FIGS. 9–11 sequentially illustrate the engagement and sealing of a fourth embodiment of the seal arrangement.
Figure 10:
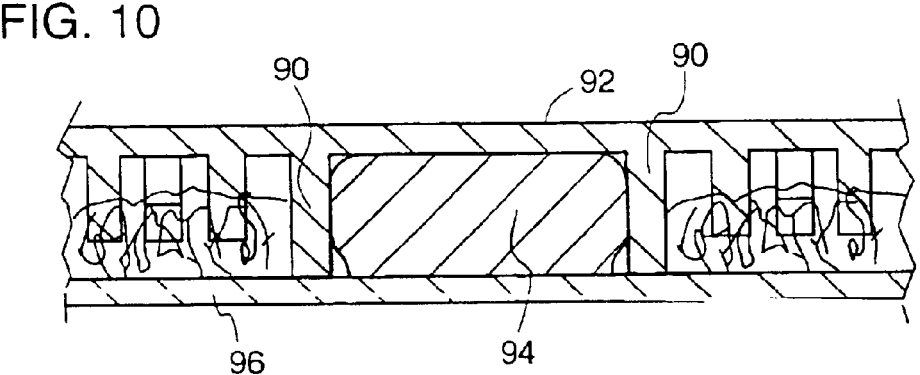

Referring now to FIG. 9, another seal arrangement has, on one side of the closure, a pair of spaced rails 90 with opposing inner sides separated by a rail spacing $S'_R$ preferably selected to be greater than the width $W'_B$ of a bead 94 of resilient material, such as closed cell foam, bonded to the base 96 of the opposing side of the closure. Longitudinally continuous rails 90 are integrally molded with base 92 and hook elements 18 by appropriately shaped mold plates in the continuous molding process described below with respect to the first illustrated embodiment. Bead 94 has a height $H_B$ from base 96 significantly greater than the combined height of the loops 16 and the hooks 18 so that engagement of the hooks 18 of the one side of the closure with the loops 16 of the opposing side of the closure necessarily causes bead 94 to interfere with base 92 of the one side of the closure. The radial outer surface 95 of bead 94 aids in aligning bead 94 between rails 90 as the closure strips are pressed together to engage the hooks and loops. As shown in FIG. 10, as closing pressure applied to the closure strips forces the hooks and loops into engagement, bead 90 is simultaneously compressed against base 92. The compression of bead 94 against base 92 causes the bead to expand laterally to bear against the inner sides of rails 90. With the hooks and loops engaged and the closing pressure released (FIG. 11), the recovery of bead 94 causes the outward deflection of base 92, which in turn cants rails 90 inward against the sides of the bead so as to maintain sealing pressure between the bead and rails as well as between the bead and base 92. Additionally, the residual compression in bead 94 creates a desirable preload tension between the hooks and loops, enhancing the performance of the closure.

Figure 11:
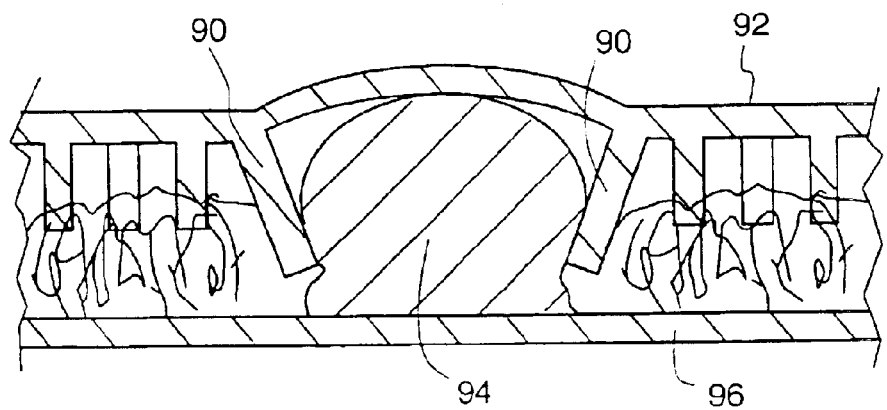

In this construction, the bead material should be sufficiently resilient that, given the selected amount of interference between bead 94 and both base 92 and rails 90, the seal will accommodate a reasonable amount of closure flexure and rail movement while maintaining a desired amount of sealing. To deflect the base of the opposing side of the closure upon recovery, as shown in FIG. 11, the bead should have sufficient shape memory as compared with the stiffness of the closure base to deflect the base slightly outward. One example of a resilient bead material is urethane foam.

Bead 94 may be jetted onto closure base 96 after the closure base has been molded in the process discussed below, or otherwise adhered to the closure base. Alternatively, the bead may be joined to resin of the base as the base is molded, as discussed below with respect to FIG. 15.

Figure 12:
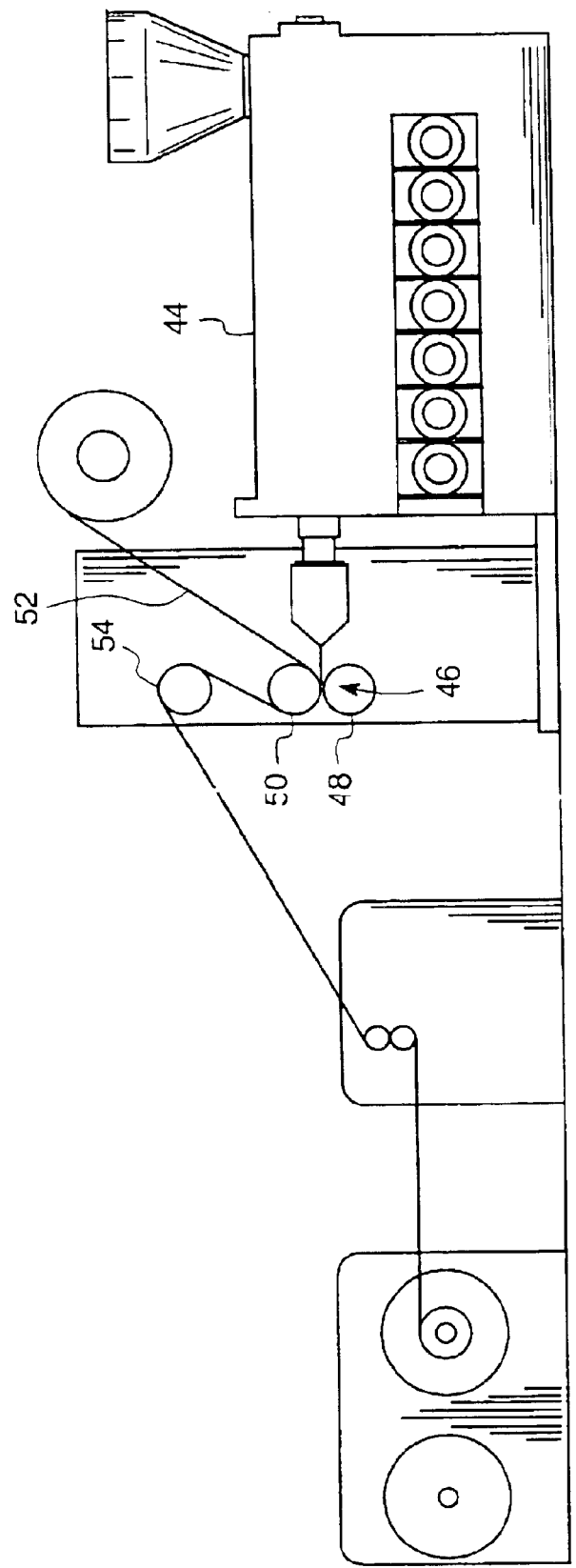
FIG. 12 illustrates a fastener strip molding apparatus and method.

Any of the hook or loop fastener strips described above may be formed in a continuous molding process as illustrated in FIG. 12. An extruder 44 supplies moldable resin at elevated temperature to a nip 46 formed between a mold roll 48 and a pressure roll 50, as taught by Fischer in U.S. Pat. No. 4,794,028, incorporated herein by reference. Alternatively, the resin may be introduced by a pressure head (not shown) to the surface of mold roll 48 under pressure. Mold roll 48 comprises many thin mold plates or rings stacked together about a central axis. For molding hook strip 14 as shown in FIG. 1, these thin mold plates also define at their common periphery an array of hook-forming cavities into which the resin is forced under pressure in the nip to mold the hook elements 18 shown in FIG. 1A. For molding loop strip 12 as shown in FIG. 1, two preformed strips of loop material 52, such as the non-woven material taught in U.S. application Ser. No. 08/922,292, now U.S. Pat. No. 6,342,285, also incorporated herein by reference, are introduced to nip 46 with the heated resin, such that the loop material becomes permanently bonded to or partially embedded in the working surface of the loop strip. The molded fastener strip is passed about a stripping roller 54 and wound for shipping.

Figure 13:
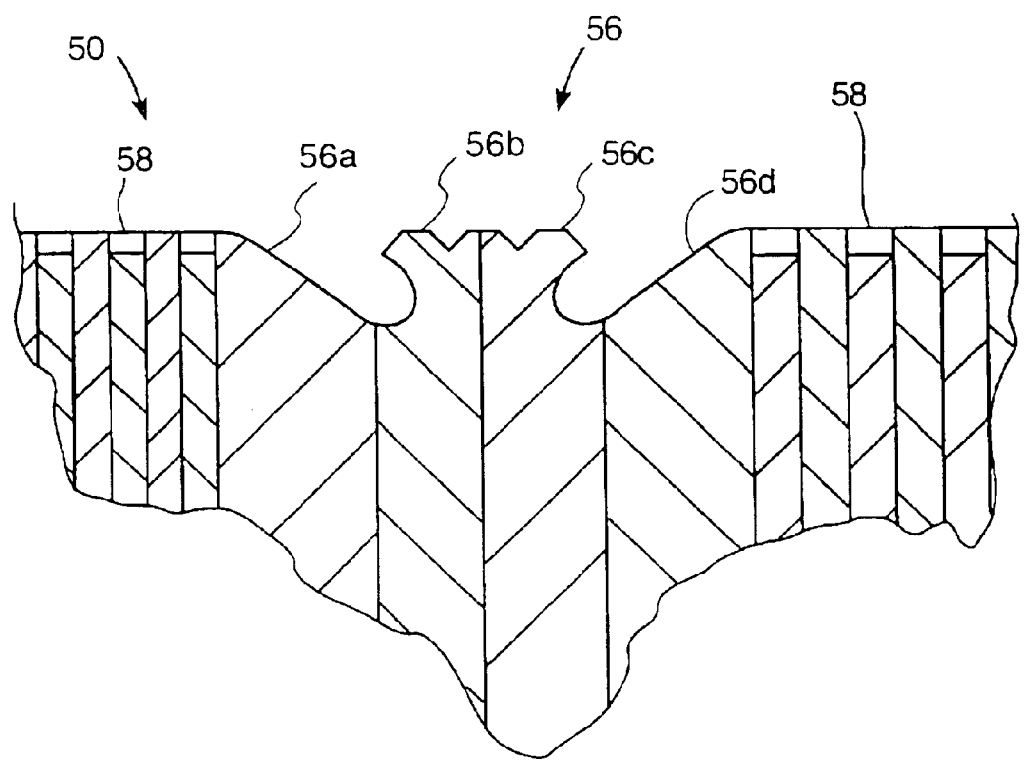
FIG. 13 is an enlarged cross-sectional view through the periphery of a mold roll configured to mold the female seal portion of FIG. 7.

FIG. 13 illustrates a partial cross-section through the periphery of mold roll 48, as configured to mold the loop strip 12' of FIG. 7. To form the female seal portion of the loop strip, a series 56 of four specially shaped mold plates 56a through 56d are provided. It should be readily apparent from FIGS. 13 and 7 how plates 56a through 56d form an appropriate molding groove for producing the illustrated female seal portion. Advantageously, plates 56b and 56c are of identical construction, mounted to face in opposite directions along the axis of the roll. The same is true about plates 56a and 56d. Thus, only two plate shapes need be produced to form the seal portion molding configuration shown. On either side of the series 56 of seal portion molding plates are plates 58 forming a pattern of features at the periphery of the mold roll for "staking" the loop material into the softened resin forming the base of the loop strip, as discussed in U.S. application Ser. No. 09/187,389, now U.S. Pat. No. 6,202,260, already incorporated by reference.

Figure 14:
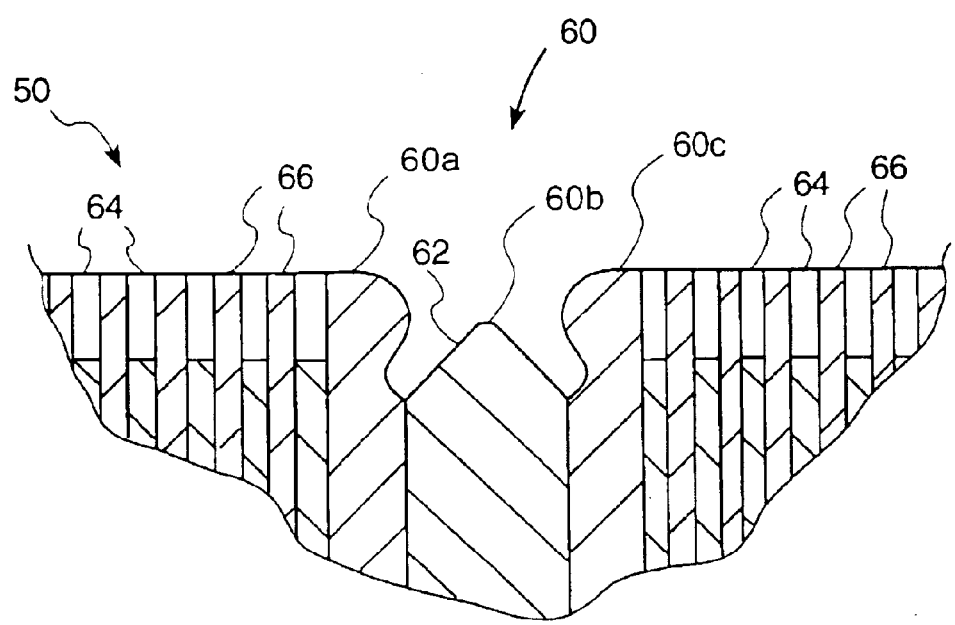
FIG. 14 is an enlarged cross-sectional view through the periphery of a mold roll configured to mold the male seal portion of FIG. 7.

By contrast, FIG. 14 shows a partial cross-section through the periphery of mold roll 48, as configured to mold the hook strip 14' of FIG. 7. The seal portion of the hook strip is formed by a series 60 of three plates (60a through 60c). Outer plates 60a and 60c are identical parts, facing opposite directions. The middle plate 60b has a raised protrusion 62 about its periphery for forming the valley between the ears of the male seal portion. On either side of this series of plates are alternating mold and spacer plates 64 and 66, respectively, for forming the arrays of hook elements.

Figure 15:
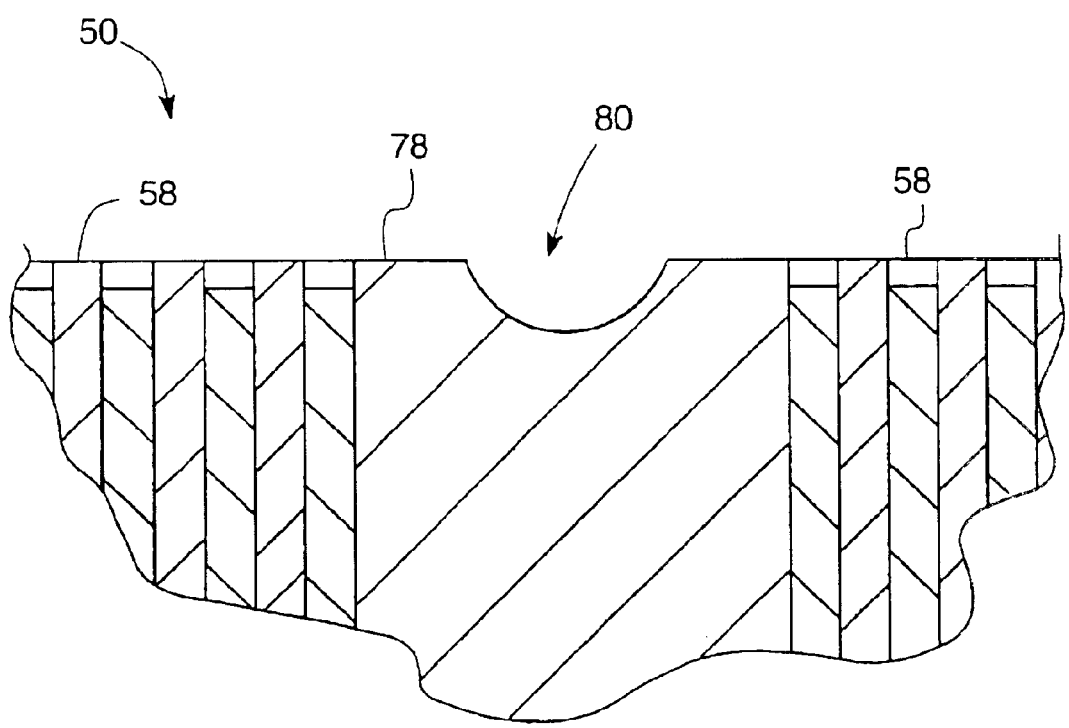
FIG. 15 is an enlarged cross-sectional view through the periphery of a mold roll configured to mold the female seal portion of FIG. 8.

FIG. 15 shows a mold plate configuration for accommodating a preformed bead of resilient material to form the loop side of the closure of FIG. 8. Sandwiched between staking plates 58 is a single center plate 78 with a groove 80 formed about its circumference. During operation, the continuous strand of resilient material that will form the seal bead is fed into the forming nip in groove 80 by being partially trained about the mold roll ahead of the nip. Groove 80 is shaped such that the resilient bead, under deformation caused by molding pressure, will sufficiently compress to enable a continuous base to be formed across the bead while, at the same time, permanently bonding one side of the bead to the base resin. In this manner, a reliable, permanent bond is formed between the base and the bead.

The mold plates for forming the seal portions of the fastener strips can be contoured by known methods, such as photo-chemical etching, electro-discharge machining, laser cutting, or traditional machining techniques.

For making unitary bag closures, both male and female seal portions may be molded simultaneously along a single fastener strip (not shown) as loop material is embedded and hooks are molded, in a process similar to the bag closure molding methods taught in U.S. application Ser. No. 09/187,389, now U.S. Pat. No. 6,202,260, on opposite sides of a central tear rib or other feature along which the closure strip is folded in the assembled bag. If desired for some applications, multiple molded profile seals may be provided across the width of a fastener strip, and may be separated by discrete bands of hooks and loops.

Moldable resins useful for forming the above fastener strips include, for example, nylons, polyesters, and both low-density and high-density polyethylenes. Advantageously, such materials are widely used in the packaging industry, such that the above-described methods can produce fastener strips of materials readily joined to bag films and other substrates, such as by thermal bonding or welding.

Besides the hook-shaped fastener elements shown in the figures, many other loop-engaging or fiber-engaging shapes may be employed, such as mushrooms, palm trees, or canted spikes. Additionally, the hooking elements need not all face in the longitudinal direction as shown, but may be formed to face in the cross-machine direction or in different directions. Other embodiments not illustrated have both an array of hooks and an array of loops on the same side of the closure, with the parallel arrays of hooks and loops separated by the seal.

A number of embodiments of the invention have been described. Nevertheless, it will be understood that various modifications may be made without departing from the spirit and scope of the invention.

What is claimed is:

1. A fastener product comprising
    a first fastener strip having
        a strip-form base with a first set of fastener elements carried on one side thereof in two spaced-apart areas; and
        extending along the base between the two areas of the first set of fastener elements, a longitudinal structure integrally molded with and protruding from said side of the base; and
    a second fastener strip having
        a strip-form base formed of a plastic resin with a second set of fastener elements carried on one side thereof in two spaced-apart areas and adapted to engage the first set of fastener elements to form a releasable fastening; and
        extending along the base between the two areas of the second set of fastener elements, a surface formed of the resin and arranged to be engaged by the longitudinal structure of the first fastener strip to form a liquid-tight seal between the fastener strips when the first and second fastener strips are engaged;
    wherein one of the first and second sets of fastener elements comprise discrete stems arranged in columns and rows, each stem integrally molded with their respective strip-form bases;
    wherein the longitudinal structure and engaged surface have complementary profiles that are adapted to interlock when the first and second fastener strips are pressed together.

2. The fastener product of claim 1 wherein at least one of the first and second sets of fastener elements comprise male, loop-engageable elements in both spaced-apart areas.

3. The fastener product of claim 1 wherein at least one of the first and second sets of fastener elements comprise engageable loops or fibers in both spaced-apart areas.

4. The fastener product of claim 1 wherein one of the spaced apart areas of fastener elements of at least one of the first and second fastener strips comprises male, loop-engageable elements, and the other of the spaced apart areas of fastener elements of the at least one of the first and second fastener strips comprises engageable loops or fibers.

5. The fastener product of claim 1 wherein the fastener elements comprising stems have heads that extend outwardly from the stems.

6. The product of claim 1 wherein the longitudinal structure comprises resin integrally molded with resin of the side of the base from which it protrudes.

7. The product of claim 1 wherein the longitudinal structure has an exposed surface of rolled form.

8. The product of claim 1 wherein the longitudinal structure and engaged surface together form an air-tight seal when the fastener strips are engaged.

9. The product of claim 1 wherein the longitudinal structure and engaged surface are held in adjacent relation by the fastener elements when the first and second fastener strips are engaged, to form a tortuous leak path.

10. The product of claim 1 wherein the complementary profiles of the longitudinal structure and engaged surface define a longitudinal cavity therebetween when the first and second fastener strips are engaged.

11. The product of claim 1 wherein the engaged surface is formed of a resilient material that is compressed upon engagement.

12. The product of claim 1 wherein the first and second sets of fastener elements together comprise hooks and hook-engageable fibers.

13. The product of claim 12 with the fastener elements of the first and second fastener strips releasably engaged, the fibers under a separating tension and the engaged surface under compression.

14. The product of claim 1 wherein the longitudinal structure of the first fastener strip and the engageable surface of the second fastener strip have engaging surfaces that are inclined at an angle to the bases of their respective fastener strips.

15. The product of claim 1 wherein the first and second fastener strips comprise a single continuous product folded over onto itself to engage the fastener elements of the fastener strips.

16. A fastener product comprising
   a first fastener strip having
      a strip-form base with a first set of fastener elements carried on one side thereof in two spaced-apart areas; and
      extending along the base between the two areas of the first set of fastener elements, a longitudinal structure integrally molded with and protruding from said side of the base; and
   a second fastener strip having
      a strip-form base with a second set of fastener elements carried on one side thereof in two spaced-apart areas and adapted to engage the first set of fastener elements to form a releasable fastening; and
      extending along the base between the two areas of the second set of fastener elements, a surface arranged to be engaged by the longitudinal structure of the first fastener strip to resist flow between the fastener strips when the first and second fastener strips are engaged;
   wherein the longitudinal structure and engaged surface have complementary profiles that define a longitudinal cavity therebetween when the first and second fastener strips are engaged.

17. The fastener product of claim 16 wherein the longitudinal structure and the engaged surface together form a liquid-tight seal when the fastener strips are engaged.

18. The fastener product of claim 16 wherein the longitudinal structure and engaged surface together form an air-tight seal when the fastener strips are engaged.

19. The fastener product of claim 16 wherein the longitudinal structure physically contacts the engaged surface when the fastener strips are engaged.

20. The fastener product of claim 16 wherein the longitudinal structure and engaged surface are adapted to interlock when the first and second fastener strips are pressed together.

21. The fastener product of claim 16 wherein the longitudinal structure and engaged surface are held in adjacent relation by the fastener elements when the first and second fastener strips are engaged to form a tortuous leak path.

22. The fastener product of claim 16 wherein the engaged surface is formed of a resilient material that is compressed upon engagement.

23. The fastener product of claim 16 wherein the first and second sets of fastener elements together comprise hooks and hook-engageable fibers.

24. The fastener product of claim 23 with the fastener elements of the first and second fastener strips releasably engaged, the fibers under a separating tension and the engaged surface under compression.

25. The fastener product of claim 16 wherein one of the first and second sets of fastener elements comprise sterns integrally molded with their respective strip-form base.

26. The fastener product of claim 16 wherein the longitudinal structure of the first fastener strip and the engageable surface of the second fastener strip have engaging surfaces that are inclined at an angle to the bases of their respective fastener strips.

27. The fastener product of claim 16 wherein the first and second fastener strips comprise a single continuous product folded over itself to engage the fastener elements of the fastener strips.

* * * * *